United States Patent
Rao et al.

(10) Patent No.: US 9,611,255 B2
(45) Date of Patent: Apr. 4, 2017

(54) PROCESS FOR TOTAL SYNTHESIS OF FLAVONOID COMPOUNDS AND ISOMERS THEREOF

(71) Applicant: COUNCIL OF SCIENTIFIC & INDUSTRIAL RESEARCH, New Dehli (IN)

(72) Inventors: Batchu Venkateswara Rao, Hyderabad (IN); Macha Lingamurthy, Hyderabad (IN); Gurrapu Raju, Hyderabad (IN); Vanka Umamaheswara Sarma, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/135,983

(22) Filed: Apr. 22, 2016

(65) Prior Publication Data
US 2016/0362401 A1    Dec. 15, 2016

(30) Foreign Application Priority Data
Jun. 10, 2015   (IN) ............................ 1741/DEL/2015

(51) Int. Cl.
| C07D 311/00 | (2006.01) |
| C07D 405/04 | (2006.01) |
| C07D 311/40 | (2006.01) |
| C07D 311/28 | (2006.01) |

(52) U.S. Cl.
CPC .......... *C07D 405/04* (2013.01); *C07D 311/28* (2013.01); *C07D 311/40* (2013.01)

(58) Field of Classification Search
CPC .... C07D 405/04; C07D 311/28; C07D 311/40
USPC ........................................................ 549/400
See application file for complete search history.

(56) References Cited

U.S. PATENT DOCUMENTS

2013/0018182 A1* 1/2013 Van der Westhuizen .. C07H 15/203 536/120

* cited by examiner

*Primary Examiner* — T. Victor Oh
(74) *Attorney, Agent, or Firm* — Hudak, Shunk & Farine Co. LPA

(57) ABSTRACT

The present invention relates to the a process for total synthesis of flavonoid compounds of general formula I and isomers thereof wherein $R_1$ and $R_2$ is OH; $R_3$=H or The present invention particularly relates to the process for preparation and separation of (2S,3S)-taxifolin-6-C-β-D-glucopyranoside (ulmoside A), (2R,3R)-taxifolin-6-C-β-D-glucopyranoside and taxifolin.

15 Claims, No Drawings

PROCESS FOR TOTAL SYNTHESIS OF FLAVONOID COMPOUNDS AND ISOMERS THEREOF

FIELD OF THE INVENTION

The present invention relates to a process for total synthesis of flavonoid compounds of general formula I and isomers thereof

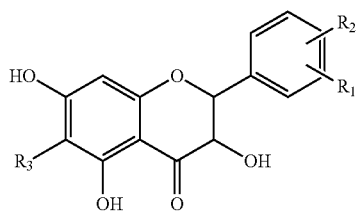

wherein $R_1$ and $R_2$ is OH; $R_3$=H, or

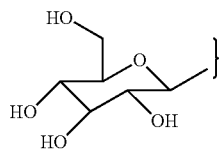

The present invention particularly relates to the process for preparation and separation of (2S,3S)-taxifolin-6-C-β-D-glucopyranoside (ulmoside A), (2R,3R)-taxifolin-6-C-β-D-glucopyranoside and taxifolin.

BACKGROUND AND PRIOR ART OF THE INVENTION

Flavonoids, one of the oldest group of natural products, they shows various bioactivities, such as radio-protective, (Goel, H. C., Kumar, I. P., Samanta, N., Rana, S. V. S. *Mol Cell Biochem.* 2003, 245, 57-67), kinase inhibitory (Yaming, X., Jeffrey, A., Smith, J. A., Deborah, A., Lannigan, D. A., Sidney, M., Hecht, S. M. *Bioorg. Med. Chem.* 2006, 14, 3974-3977) and apoptotic activities related to cancer (Brusselmans, K., Vrolix, R., Verhoeven, G., Swinnen, J. V. *J. Biol. Chem.* 2005, 280, 5636-5645). They show antioxygenic and metal chelating activities (Gao, X. In Seabuckthorn, Hippophae L. Biochemistry and Pharmacology.; Singh, Virendra, Ed., Daya Publishing House: Delhi, 2006; Vol. II, pp 390-401), and have also been implicated in the conditions related to degenerative diseases (aging), wound healing and cardio-vascular problems. Recently exploiting flavonoids as candidates for prevention and treatment of osteoporosis have been gaining importance. Flavanoids having O-glycoside moiety show lot of interesting biological activities. For example rutin (quercetin-3-O-glucose rhamnose) inhibits the ovariectomy-induced resorption of bone in rats (Horcajada-Molteni, M.-N., Crespy, V., Coxam, V., Davicco, M.-J., Remesy, C., Barlet, J.-P. *J. Bone Miner. Res.* 2000, 15, 2251-2258). Quercetin which is a aglycon of rutin has been reported to inhibit the osteoclastic resorption of bone in vitro (Wattel, A., Kamel, S., Mentaverri, R., Lorget, F., Prouillet, C. Petit, J.-P., Fardelonne, P., Brazier, M. *Biochem. Pharmacol.* 2003, 65, 35-42; Notoya, M., Tsukamoto, Y., Nishimura, H., Woo, J.-T., Nagai, K., Lee, I.-S., Hagiwara, H. *Eur. J. Pharmacol.* 2004, 485, 89-96). But these 0-glycosides susceptible to undergo cleavage of glycosyl bond to give glycon and aglycon moieties in the biological system, therefore their stability in the biological system is questionable. Recently Rakesh mourya et. al isolated and identified three new C-glycosylated flavonoids considered as stable glycosides in the biological system namely (2S,3S)-(+)-3',4',5,7-tetrahydroxydihydroflavonol-6-C-β-D-glucopyranoside, (2S,3S)-(+)-4',5,7-trihydroxy dihydro flavonol-6-C-β-D-glucopyranoside and 3-C-β-D-glucopyranoside-2,4,6-trihydroxymethylbenzoate from ulmus wallichiana plant (Rawat, Preeti; Kumar, Manmeet, Sharan, Kunal; Chattopadhyay, Naibedya; Maurya, Rakesh. *Bioorg. Med. Chem. Lett.* 2009, 19, 4684-4687) (WO 2009110003 A1). Which is known in traditional Indian medicinal practice to treat the bone fracture and assessed their activity in stimulating osteoblast differentiation. Stimulating of osteoblast differentiation is a bone anabolic function that is desirable for osteoporosis therapy. (2S,3S)-Taxifolin-6-C-β-D-glucopyranoside also known as ulmoside A or K058 is showing excellent bone deflecting activity.

(2R,3R)-Taxifolin-6-C-β-D-glucopyanoside is a natural product isolated from the medicinal plant *Garcinia epunctata* and a tree from *Garcinia buchananii* bark. This compound shows extraordinarily high antioxidative power {(Stark, T.; Matsutomo, T.; Losch, S.; Boakye, P.; Balemba, O.; pasilis, S.; Hofmann, T. *J. Agric. Food Chem.* 2012, 60, 2053-2062); (Mbafor, J. T.; Fomum, Z. T.; Promsattha, B.; Sanson, D. R.; Tempesta, M. S. *J. Nat. Prod.* 1989, 52, 417-419)}.

The above two compounds can only be obtained from the natural source in very small quantities. More over evaluation of their biological activity to develop into the drug requires more quantities of compound, for this a simple short and scalable strategy is indeed essential.

So far there are no reports on the synthesis of these compounds in the literature. Although there are some reports on the synthesis of flavone 6-C-β-D-gluco compounds (*Carbohydrate Research.* 2010, 345, 1825-1830) (WO 2011064726 A1) but so far there is no report of the synthesis of title compounds 1 and 2. Herein we are presenting the first total synthesis involving highly regioselective glycosidation of (−)-taxifolin and (+)-taxifolin to give the compounds ulmoside A (1) and (2R,3R) taxifolin6-C-β-D-glucopyranoside (2).

Structures of Some Flavonoids and O- and C-Glycosides of Flavonoids:

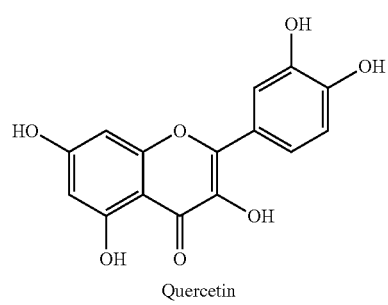
Quercetin

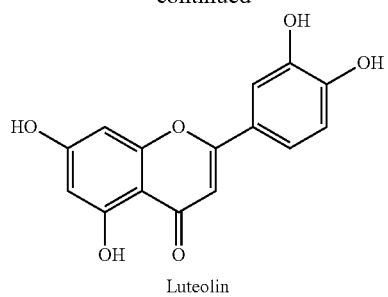
Luteolin
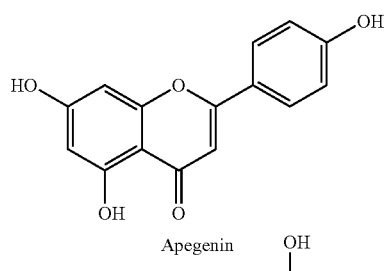
Apegenin
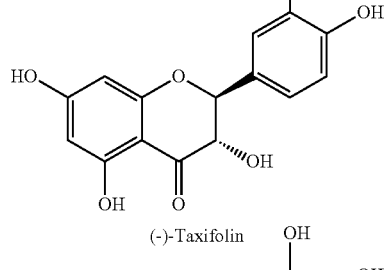
(−)-Taxifolin
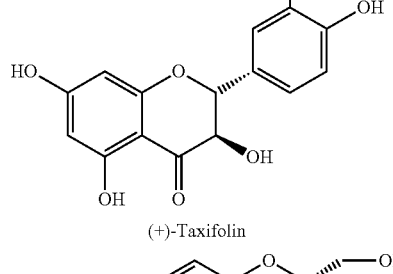
(+)-Taxifolin
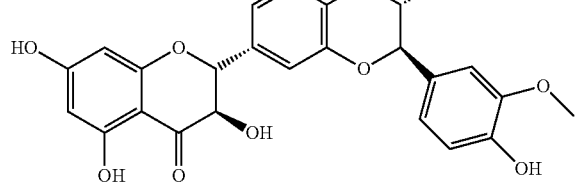
Silybin
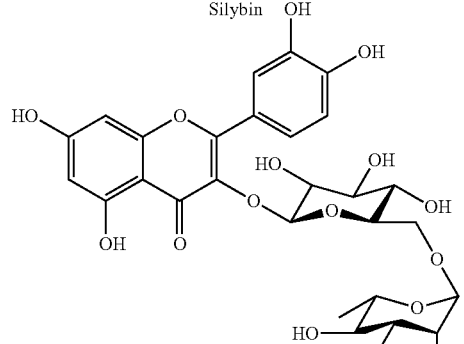
Rutin
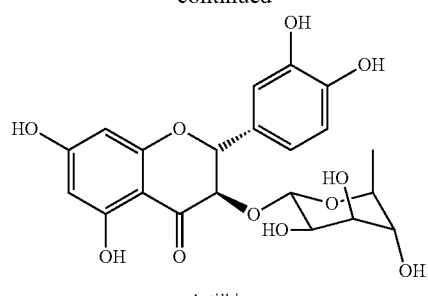
Astilbin
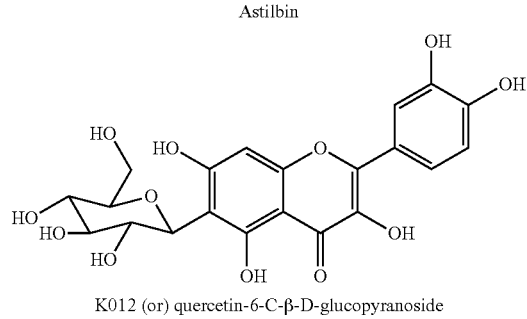
K012 (or) quercetin-6-C-β-D-glucopyranoside
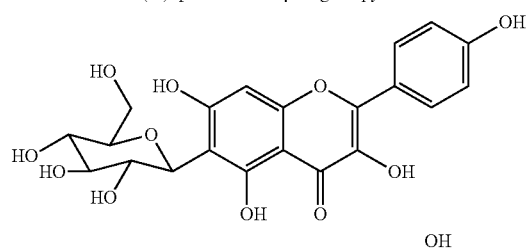
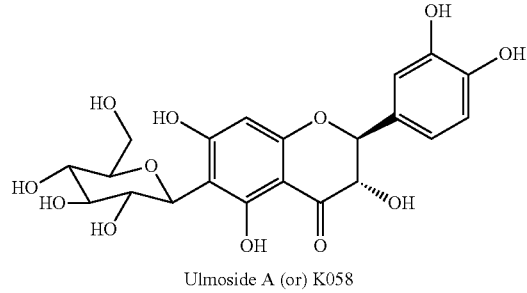
Ulmoside A (or) K058
(2S, 3S) Taxifolin-6-C-β-D-glucopyranoside
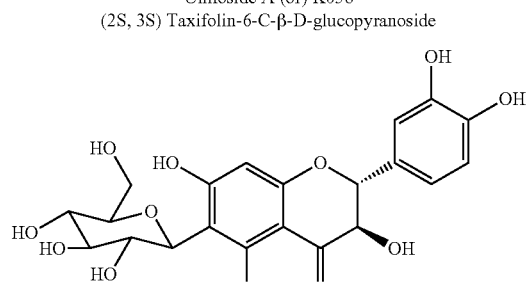
(2R, 3R) Taxifolin-6-C-β-D-glucopyranoside
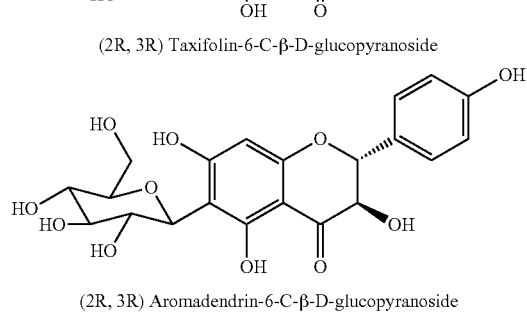
(2R, 3R) Aromadendrin-6-C-β-D-glucopyranoside

OBJECTIVES OF THE INVENTION

The main object of the present invention is to provide a process for total synthesis of flavonoid compounds and isomers thereof.

Another object of the present invention is to provide a process for preparation of (2S,3S)-taxifolin-6-C-β-D-glucopyranoside (ulmoside A) and (2R,3R)-taxifolin-6-C-β-D-glucopyranoside.

Yet another object of the present invention is to provide a process for separation of isomers (2S,3S)-taxifolin-6-C-β-D-glucopyranoside (ulmoside A) and (2R,3R)-taxifolin-6-C-β-D-glucopyranoside.

One more object of the present invention is to provide a process for the synthesis of (−)taxifolin and (+)taxifolin.

Further object of the present invention is to provide an isolation and purification of individual isomers.

SUMMARY OF THE INVENTION

Accordingly, the present invention provides a process for total synthesis of flavonoid compounds of general formula I and isomers thereof,

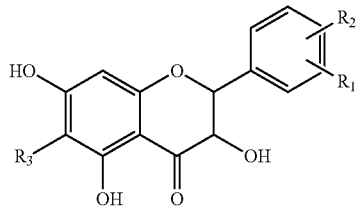

I wherein $R_1$ and $R_2$ is OH; $R_3$=H, or

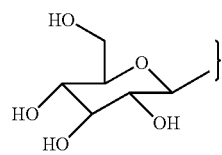

In an embodiment the present invention, wherein the present invention provides a process for total synthesis of flavonoid compounds of general formula I and isomers thereof, comprising the steps of:

i. protecting the hydroxyl groups of phloroglucinol and hydroxyl groups of caffeic acid as ethers by using protecting group and base in a solvent to get 1,3,5-tris (methoxymethoxy) benzene (5) and (E)-methyl3-(3,4-dihydroxyphenyl) acrylate (6) respectively;

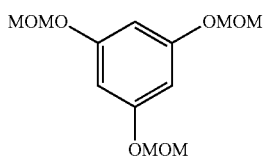

5

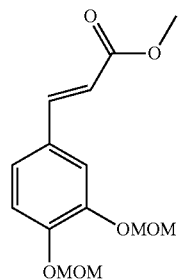

6 where MOMO is methoxymethoxy and OMOM is also methoxymethoxy;

ii. hydrolysing of the (E)-methyl 3-(3,4-dihydroxyphenyl) acrylate (6) obtained in step (i) by using hydrolysing agent to get (E)-3-(3,4-bis(methoxymethoxy) phenyl) acrylic acid (7);

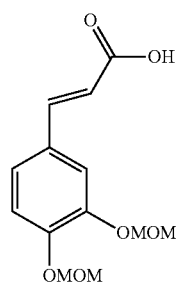

7 iii. acylating the 1,3,5-tris(methoxymethoxy)benzene (5) and (E)-3-(3,4-bis (methoxymethoxy) phenyl)acrylic acid (7) obtained in steps (i & ii) in presence of acylating agent in a solvent at a temperature ranging between −5° C. to 0° C. to get (E)-3-(3,4-bis (methoxymethoxy)phenyl)-1-(2,4,6-tris (methoxymethoxy)phenyl) prop-2-en-1-one (8);

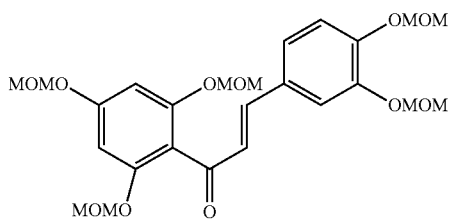

8 iv. oxidising (E)-3-(34-bis(methoxymethoxy)phenyl)-1-(2,4,6-tris(methoxymethoxy) phenyl)prop-2-en-1-one (8) obtained in step (iii) with oxidising agent to get racemic epoxide ((3(3,4bis(methoxymethoxy)phenyl) oxiran2yl)(2,4,6tris(methoxy methoxy)phenyl) methanone) (9);

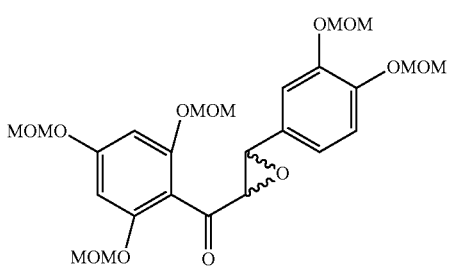

v. reacting the epoxide compound ((3(3,4bis(methoxymethoxy)phenyl)oxiran2yl)(2,4,6tris(methoxymethoxy)phenyl)methanone) (9) obtained in step (iv) by using excess of acid in different ratio of mixture of solvent ranging in the ratio 1:0/0:1 to 5:1/1:5 to obtain racemic taxifolin 2-(3,4-dihydroxyphenyl)-3,5,7-trihydroxychroman-4-one(+/−Taxifolin) (10);

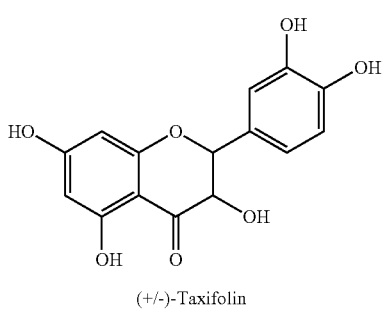

(+/-)-Taxifolin vi. optionally separating the racemic (+/−taxifolin) 2-(3,4-dihydroxyphenyl)-3,5,7-trihydroxychroman-4-one by chromatographic method to obtain (−) taxifolin and (+) taxifolin (11) and (12);

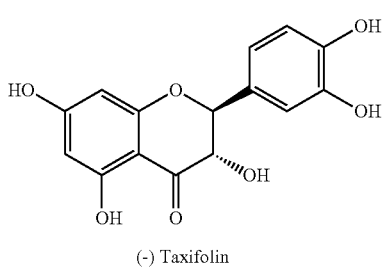

(-) Taxifolin

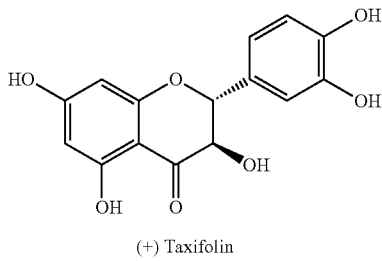

(+) Taxifolin refluxing the racemic or (+)taxifolin or (−)taxifolin obtained in steps (v) and (vi) in a solvent and D-glucose in presence of a Lewis acid at a temperature ranging between 85° C. to 90° C. for a period ranging between 24 h to 48 hr to get distereomeric mixture of taxifolin-glucopyranosides or (2R,3R)-Taxifolin-6-C-beta-D-Glucopyranoside or Ulmoside A respectively; separating the distereomeric mixture of taxifolin-glucopyranosides to obtain (2R,3R) taxifolin-6-C-β-D-glucopyranoside and (2S,3S) taxifolin-6-C-β-D-glucopyranoside (ulmoside A) pure product.

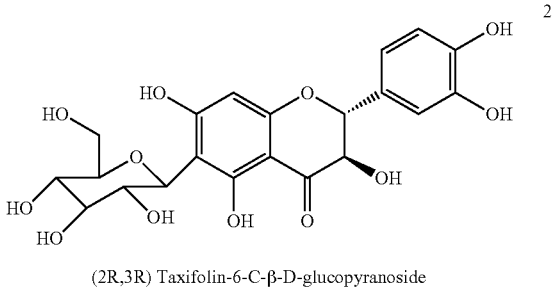

(2R,3R) Taxifolin-6-C-β-D-glucopyranoside

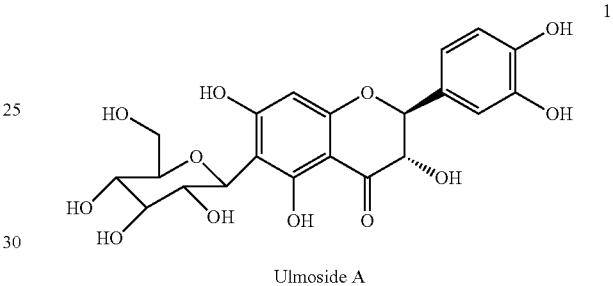

Ulmoside A

In another embodiment of the present invention, wherein the base is selected from the group consisting of NaH, NaNH$_2$, KH, KNH$_2$, MeONa, EtONa, iPrONa and t-BuOK.

In yet another embodiment of the present invention, wherein the acid is selected from the group consisting of ZnCl$_2$, BF$_3$.OEt$_2$, Zr(OTf)$_2$ and FeCl$_3$.

In yet another embodiment of the present invention, wherein the reagent used for protecting hydroxyl group in step (i) is selected from the group consisting of methoxymethylchloride, 2-methoxyethoxymethyl chloride (or) 2-methoxyethylacetate, dimethoxymethane and t-butyldimethylsilyl chloride, t-butyldiphenylsilyl chloride.

In still another embodiment of the present invention, wherein the solvent used in step (i) is selected from the group consisting of DMF, THF, Et$_2$O, 1,4 dioxane, diisopropylether and t-Butyl ethyl ether.

In another embodiment of the present invention, wherein the hydrolysing agent is selected from the group consisting of NaOH, KOH, LiOH, Cs$_2$CO$_3$ in a solvents like MeOH, EtOH, iPrOH, MeOH/THF, EtOH/THF and Dioxane/H$_2$O.

In yet another embodiment of the present invention, wherein the acylating agent used is selected from the group consisting of TFAA (trifluroaceticanhydride).

In another embodiment of the present invention, wherein the solvent used in step (iii) for acylating agent is selected from the group consisting of DCM (Dichloromethane), DCE (1,2-dichloroethane) and CCl$_4$.

In still another embodiment of the present invention, wherein the oxidation of compound is done by using the reagent comprising of hydrogen peroxide and a base selected from the group consisting of NaOH, KOH, TBHP (tert-Butyl hydroperoxide) in presence of NaH or DBU (1,8-Diazabicyclo[5.4.0]undec-7-ene) or KH.

In another embodiment of the present invention, wherein the acid used in step (v) is selected from the group consisting of concentration HCl and H$_2$SO$_4$.

In yet another embodiment of the present invention, wherein the solvent used in step (v) is selected from the group consisting of MeOH, EtOH, iPrOH, MeOH, EtOH, iPrOH, THF and mixture thereof.

In another embodiment of the present invention, wherein different ratio of mixture of solvent used in step (vi) is selected from the group like CH$_3$CN/H$_2$O, EtOH/H$_2$O, THF/H$_2$O.

In still another embodiment of the present invention, wherein the Lewis acid is M(X)$_3$ where M=Lanthanides such as La, Ce, Pr, Nd, Sm, Eu, Gd, Tb, Dy, Ho, Er, Tm; M=Metal such as Sc, Cd, Fe, Al, Cr, Co, Ni, Cu, Zn, Rh, Ag and X=OTf, Cl, ClO$_4$.

In another embodiment of the present invention, wherein the chromatographic method used for separation for distereomeric mixture of taxifolin or taxifolin-glucopyranosides is selected from the group consisting of HPLC, UPLC, UFLC and MPLC.

In another embodiment of the present invention, wherein the representative flavonoid compounds prepared by the process comprising:

10

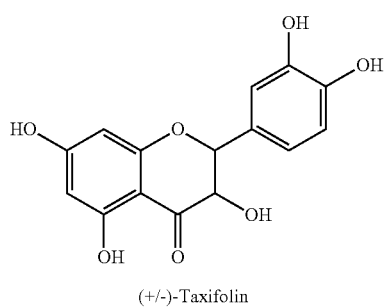

(+/-)-Taxifolin

11

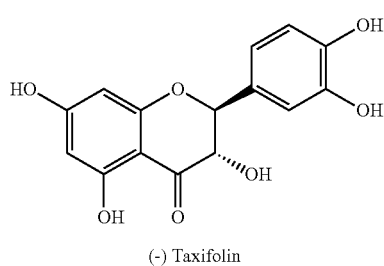

(-) Taxifolin

12

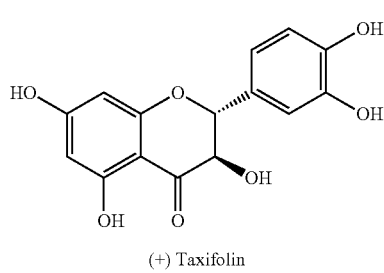

(+) Taxifolin

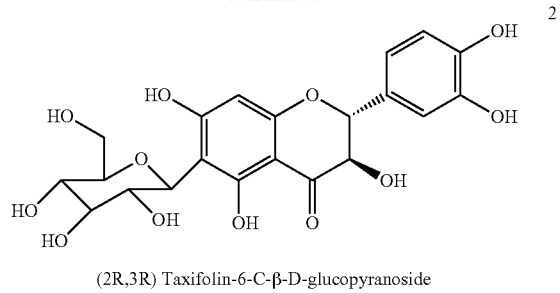

(2R,3R) Taxifolin-6-C-β-D-glucopyranoside

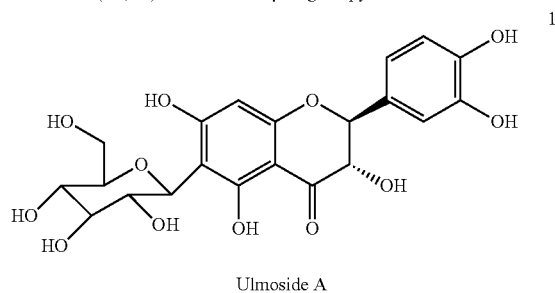

Ulmoside A

DETAILED DESCRIPTION OF THE INVENTION

The key intermediate in synthesis of taxifolin is chalcone. It was prepared by acylation of 1,3,5-tris(methoxymethoxy)benzene with (E)-3-(3,4-bis(methoxymethoxy)phenyl)acrylic acid using mixed anhydride method. Epoxidation of the chalcone using hydrogen peroxide and sodium hydroxide gave racemic epoxide (Yang, L. X.; Huang, K. X.; Li, H. B.; Gong, J. X.; Wang, F.; Feng, Y. B.; Tao, Q. F.; Wu, Y. H.; Li, X. K.; Wu, X. M.; Zeng, S.; Spencer, S.; Zhao, Y.; Qu, J. *J. Med. Chem.* 2009, 52, 7732-7752), which was subjected to excess acid undergoes cyclisation to give (+/−) taxifolin.

The chiral HPLC method was developed for separation of (+/−)-taxifolin.

(−)-Taxifolin was subjected to glycosidation in presence of Lewis acid with D-glucose to give ulmoside A.

(+)-Taxifolin was subjected to glycosidation in presence of Lewis acid to give the corresponding (2R,3R) (+)-taxifolin 6-C-β-D-glucopyranoside.

(+/−)-Taxifolin was subjected to glycosidation in presence of Lewis acid to give the corresponding mixture of ulmoside A and (2R,3R) (+)-taxifolin 6-C-β-D-glucopyranoside The HPLC method was developed for the separation of ulmoside A and (2R,3R) taxifolin-6-C-β-D-glucopyanoside.

Chalcone is the key intermediate for the synthesis of taxifolin. We have synthesized the chalcone from less expensive starting materials phloroglucinol and caffeic acid. The synthesis of chalcone as shown in scheme 1 comprises following steps.

The process for the preparation of 1,3,5-tris(methoxymethoxy)benzene (5) and the said process comprising the steps of:

i. Phloroglucinol (3) was dissolved in DMF then NaH was added at 0° C.

ii. The reaction mixture was stirred for 10 min then MOMCl was added at −5° C., where MOMCl is methoxymethyl chloride.

iii. The mixture was stirred for 5 h.

iv. The reaction mixture was quenched with saturated ammonium chloride solution.
v. Purifying by column chromatography using ethyl acetate-hexane gave the 1,3,5-tris(methoxymethoxy) benzene (5).

The process for the preparation of (E)-methyl 3-(3,4-dihydroxyphenyl) acrylate (6) and the said process comprising the steps of:
  i. Caffeic acid (4) was dissolved in MeOH then catalytic amount of $H_2SO_4$ was added.
  ii. The reaction mixture was stirred for 1 h at r.t and then the solvent was removed under reduced pressure.
  iii. The crude was dissolved in DMF and NaH and MOMCl were added at 0° C.
  iv. The reaction mixture was stirred for overnight.
  v. The reaction was quenched with saturated ammonium chloride solution.
  vi. Purification by column chromatography using ethyl acetate-hexane gave the (E)-methyl 3-(3,4-dihydroxyphenyl)acrylate (6).

The process for the preparation of (E)-3-(3,4-bis (methoxymethoxy)phenyl)acrylic acid (7) and the said process comprising the steps of:
  i. Compound (9) was dissolved in MeOH and THF and NaOH was added.
  ii. The reaction mixture was stirred for overnight.
  iii. The solvent was removed under reduced pressure extracted with ethyl acetate and water, and washed with 1N HCl.
  iv. Purifying by column chromatography using ethyl acetate-hexane gave the (E)-3-(3,4-bis (methoxymethoxy)phenyl)acrylic acid (7).

The process for the preparation of (E)-3-(3,4-bis (methoxymethoxy)phenyl)-1-(2,4,6-tris(methoxymethoxy) phenyl)prop-2-en-1-one (8) and the said process comprising the steps of:
  i. Compound (7) was dissolved in DCM then triflouro acetic anhydride (TFAA) was added drop wise at −5° C.
  ii. The reaction mixture was stirred for 5 min.
  iii. Then compound (5) in DCM was added at −5° C.
  iv. The reaction mixture was quenched with saturated ammonium chloride solution after 30 min.
  v. Purifying by column chromatography using ethyl acetate-hexane gave the (E)-3-(3,4-bis (methoxymethoxy)phenyl)-1-(2,4,6-is (methoxymethoxy)phenyl) prop-2-en-1-one (8).

The process for the preparation of (3(3,4bis (methoxymethoxy)phenyl) oxiran-2-yl) (2,4,6 tris (methoxymethoxy) phenyl) methanone (9) and the said process comprising the steps of
  i. To a stirring solution of (8) in MeOH was added, 2N NaOH solution and 30% $H_2O_2$.
  ii. The reaction was stirred at room temperature for 5 h, monitored by TLC.
  iii. The reaction was then evaporated, the residue was partitioned between 50 mL of water and ethyl acetate.
  iv. The organic layer was dried ($Na_2SO_4$), filtrated, and the resulted solution was subjected to next step directly.

The process for the preparation of 2-(3,4-dihydroxyphenyl)-3,5,7-trihydroxychroman-4-one (15), viz (+/−)-taxifolin (10) and the said process comprising the steps of
  i. To a stirred solution of above-mentioned epoxide (9) in MeOH and THF was added, concentrated HCl in methanol.
  ii. The reaction was maintained at 55° C. for 2 h.
  iii. After evaporation of most of the solvent, the mixture was extracted by ethyl acetate.
  iv. The organic layer was washed successively by water and brine ($Na_2SO_4$), dried.
  v. The filtrate was evaporated to give a residue which was subjected to a column chromatography with $CHCl_3$/MeOH 10:1 as eluent.

The process for the separation of (+/−)-taxifolin (10) using chiral HPLC method:
  i. For the separation of (+/−) taxifolin chiral HPLC was carried out using isopropyl alcohol and hexane at the ratio of 20:80, at the flow rate of 1.0 ml/min using chiral pack IC column with dimension 250×4.6 mm, 5µ lit.
  ii. Preparation chromatography was carried out for the separation of individual isomers using mobile phase which consists of 20% IPA and 80% hexane at the flow rate of 2 ml/min. Chiral pack IC column with dimension 250×10.0 mm with 5µ lit particle was used and the detection was performed at 210 nm.
  iii. The separation was carried out using mobile phase consists of acetonitrile and water at the ratio of 20:80 with 0.1% formic acid as additive. The column used was phenomenax lux C4 250×4.6 mm, 5µ lit and the detection was performed at 210 nm.

The process for the preparation of (2S,3S) (+)-taxifolin-6-C-β-D-glucopyranoside (1) and the said process comprising the steps of
  i. A solution of (−) taxifolin (11) and D-glucose in 2:1 $CH_3CN$—$H_2O$ was refluxed for 48 h in the presence of $Sc(OTf)_3$.
  ii. Which was purified by silica-gel column chromatography (15:30:2:0.1 acetone-ethyl acetate —$H_2O$— AcOH) to give 1 as a white amorphous powder.

The process for the preparation of (2R,3R) (+)-taxifolin-6-C-β-D-glucopyranoside (2) and the said process comprising the steps of
  iii. A solution of (+) taxifolin (12) and D-glucose in 2:1 $CH_3CN$—$H_2O$ was refluxed for 48 h in the presence of $Sc(OTf)_3$.
  iv. Which was purified by silica-gel column chromatography (15:30:2:0.1 acetone-ethyl acetate —$H_2O$— AcOH) to give 1 as a white amorphous powder.

The process for the preparation of diastreomeric mixture of ulmoside A (1) and (2R,3R) (+)-taxifolin-6-C-β-D-glucopyranoside (2) and the said process comprising the steps of
  i. A solution of (+/−)-taxifolin (10) and D-glucose in 2:1 $CH_3CN$—$H_2O$ was refluxed for 48 h in the presence of $Sc(OTf)_3$.
  ii. Which was purified by silica-gel column chromatography (15:30:2:0.1 acetone-ethyl acetate —$H_2O$— AcOH) to give diastreomeric mixture of ulmoside A (1) and (2R,3R) (+)-taxifolin-6-C-β-D-glucopyranoside (2) as a white amorphous powder.

The process for the separation of diastereomeric mixture of ulmoside A and (2R,3R)-taxifolin-6-C-β-D-glucopyanoside by using chiral HPLC method:
  i. Procedure for the separation of diastereomeric mixture of ulmoside A and (2R,3R)-taxifolin-6-C-β-D-glucopyanoside.
  ii. HPLC was carried out in which acetonitrile and water was used as mobile phase in a gradient run at the flow rate of 1.0 ml/min and the detection of the isomers was performed at 290 nm using Diode Array Detector. Total retention was 35 minutes Part A Preparation of Racemic Mixture of (2S,3S) and (2R,3R) Taxifolin Scheme 1:

Chalcone is the key intermediate for the synthesis of taxifolin. We have synthesized the chalcone from less expensive starting materials phloroglucinol and caffeic acid. The synthesis of chalcone as shown in scheme 1 comprises following steps.

dized using known procedure with alkaline hydrogen peroxide and 2N NaOH which led to smooth formation of racemic epoxide 9. Initially the epoxide was treated with concentrated HCl in MeOH and THF (2:1) solvent using reported literature (Yang, L. X.; Huang, K. X.; Li, H. B.; Gong, J. X.; Wang, F.; Feng, Y. B.; Tao, Q. F.; Wu, Y. H.; Li, X. K.; Wu, X. M.; Zeng, S.; Spencer, S.; Zhao, Y.; Qu, J. *J. Med. Chem.* 2009, 52, 7732-7752) resulted in mixture of compounds. Modification of the above procedure in presence of excess acid smoothly gave the required (+/−) taxifolin 10 with 73% yield.

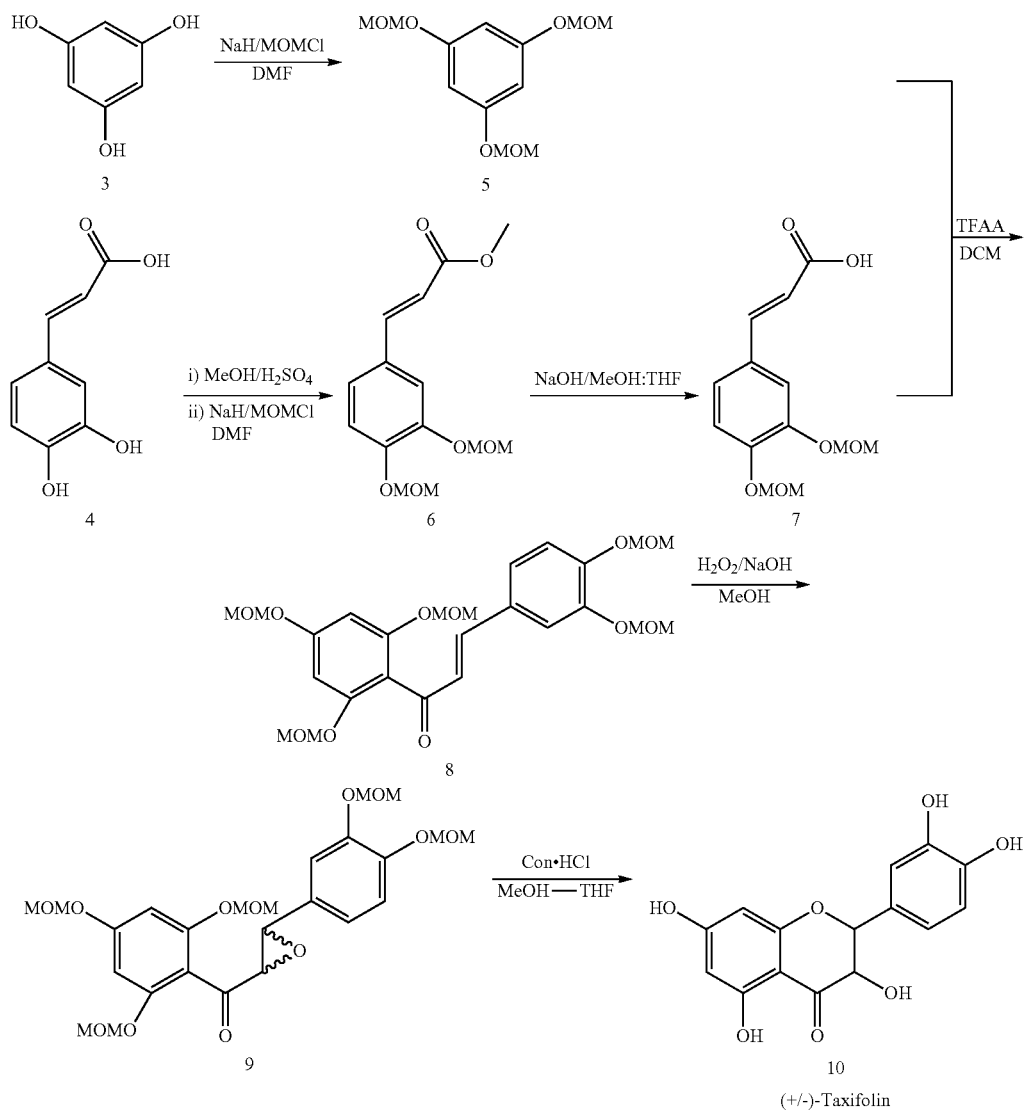

First the hydroxyl groups of phloroglucinol protected as MOM ethers gave compound 5. Caffeic acid 4 is subjected to acid catalysed esterfication using $H_2SO_4$ in methanol. Then the crude ester was treated with MOMCl and NaH in DMF solvent to protect the phenolic alcohols as MOM ethers to give the compound 6. The compound 6 was converted to acid 7 which is useful for the acylation by mixed anhydride method. Further the acylation of compound 5 with compound 7 in presence of TFAA (trifluroaceticanhydride) in DCM at −5° C. gave the known chalcone 8 with 50% yield. Further the chalcone was oxi- Part B HPLC Procedure for the Separation of (+/−) Taxifolin to (+) Taxifolin and (−) Taxifolin.

Method 1:

For the separation of (+/−)-taxifolin chiral HPLC was carried out using isopropyl alcohol and hexane at the ratio of 20:80, at the flow rate of 1.0 ml/min using chiral pack IC column with dimension 250×4.6 mm, 5μ lit.

Preparation chromatography was carried out for the separation of individual isomers using mobile phase which consists of 20% IPA and 80% hexane at the flow rate of 2 ml/min. Chiral pack IC column with dimension 250×10.0 mm with 5µ lit particle was used and the detection was performed at 210 nm.

Method 2:

The separation was carried out using mobile phase consists of acetonitrile and water at the ratio of 20:80 with 0.1% formic acid as additive. The column used was phenomenax lux C4 250×4.6 mm, 5µ lit and the detection was performed at 210 nm. The optical rotation and spectral data of (+)-taxifolin was in accordance with the reported values (T. Kikuchi, T.; Nishimura, M.; Hoshino, A.; Morita, Y.; Iida, S.; Saito, N.; Honda, T. *Heterocycles*. 2003, 60, 1469-1475).

Part C

General Procedure for C-Glycosidation:

Direct C-glycosidation of (+) (2S,3S) taxifolin-6-C-β-D-glucopyranoside (ulmoside A) was performed as follows. An aqueous $CH_3CN$ solution (2:1 $CH_3CN—H_2O$) of (−) taxifolin (1 equiv) and D-glucose (2.5 equiv) was refluxed in an oil bath (85° C.) for 48 h in the presence of 0.4 equiv of $Sc(OTf)_3$. Which was subjected to silica-gel column chromatography (15:30:2:0.1 acetone-ethyl acetate —$H_2O$—AcOH). As a result of this experiment, ulmoside A was afforded as a white amorphous powder in 35% yield.

Preparation of (2S,3S) taxifolin-6-C-β-D-glucopyranoside (ulmoside A) from (−) taxifolin and D-glucose Scheme 2:

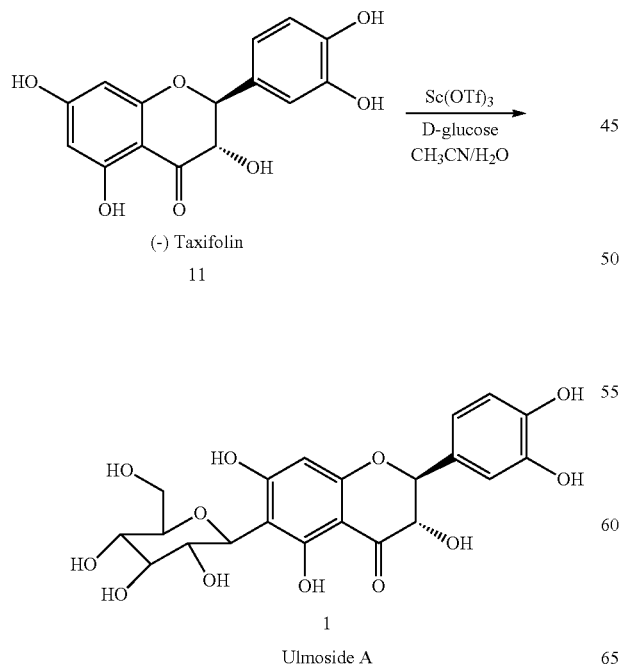

Ulmoside A

Preparation of (2R,3R) taxifolin-6-C-β-D-glucopyranoside from (+) taxifolin and D-glucose Scheme 3:

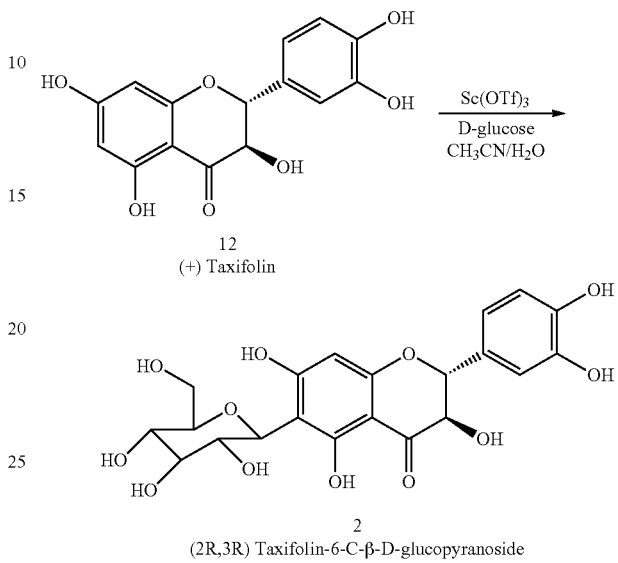

Preparation of diastereomeric mixture of ulmoside A and (2R,3R) taxifolin-6-C-β-D-glucopyranoside from (+/−) taxifolin and D-glucose Scheme 4:

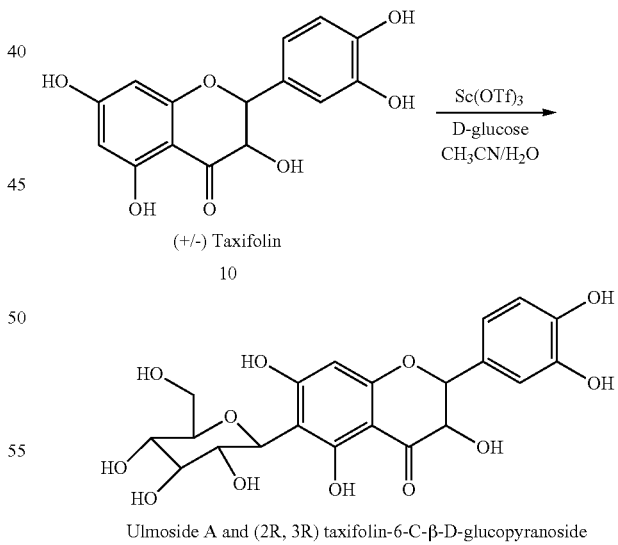

Ulmoside A and (2R, 3R) taxifolin-6-C-β-D-glucopyranoside

Part D

Procedure for the Separation of Diastereomeric Mixture of Ulmoside a and (2R,3R) Taxifolin-6-C-β-D-Glucopyranoside Analysis of the sample was carried out on M/s Agilent 1100 series High Performance Liquid Chromatography Germany. Due to the complexity involved in the separation of this diastereomeric mixture several conditions were tried out. Ultimately considerable separation was achieved on Gemini NX 250×4.6 mm column. The particle size of the stationary phase was 5μ. Mixture of acetonitrile and water with addition of 0.1% formic acid in a gradient elution pattern as prescribed below was used as mobile phase at the flow rate of 1.0 mL/min.

| Time | % B |
| --- | --- |
| 0.0 | 0.0 |
| 5.0 | 0.0 |
| 25.0 | 20.0 |
| 26.0 | 0.0 |
| 35.0 | 0.0 |

Solvent A: Water (0.1% Formic acid)
Solvent B: Acetonitrile (0.1% Formic acid)
Column: Gemini NX 250×4.6 mm, 5μ.
Flow rate: 1.0 ml/min
Detection: 290 nm The detection of these isomers was made at 290 nm using Diode Array Detector. Synthesized sample of each isomer in pure form and mixture of both isomers was injected and confirmed the presence of isomers in the sample mixture. Mass spectrometer was hyphenated with HPLC as additional detector for the identification of the isomers in the sample. Total retention was 35 minutes. The spectral data of ulmoside A and (2R,3R) taxifolin-6-C-β-D-glucopyranoside were in accordance with the reported values {(Rawat, Preeti; Kumar, Manmeet, Sharan, Kunal; Chattopadhyay, Naibedya; Maurya, Rakesh. *Bioorg. Med. Chem. Lett.* 2009, 19, 4684-4687); (Stark, T.; Matsutomo, T.; Losch, S.; Boakye, P.; Balemba, O.; pasilis, S.; Hofmann, T. *J. Agric. Food Chem.* 2012, 60, 2053-2062)}.

EXAMPLES

The following examples, which include preferred embodiments, will serve to illustrate the practice of this invention, it being understood that the particulars shown are by way of examples and for purpose of illustrative discussion of preferred embodiments of the invention only and are not limiting the scope of the invention Example-1

1,3,5-tris(methoxymethoxy)benzene (5)

Phloroglucinol (3) (2.0 g 15.8 mmol) was dissolved in DMF then NaH (2.8 g 71.4 mmol) was added at 0° C. The reaction mixture was stirred for 10 min then MOMCl (5 ml, 63.4 mmol) was added at −5° C. and the mixture was stirred for 5 h. The reaction mixture was quenched with saturated ammonium chloride solution, and extracted with ethyl acetate and water. The solvent was evaporated under reduced pressure. The crude was purified by column chromatography using ethyl acetate and hexane to give 5 (4.0 g, 97%). $^1$H NMR: (500 MHz, CDCl$_3$) δ 3.44 (9H, s), 5.12 (6H, s), 6.48 (3H, s). $^{13}$C NMR: (125 MHz, CDCl$_3$) δ 56.0, 94.4, 98.3, 158.8. ESIMS: m/z 259.

Example-2

(E)-methyl 3-(3,4-dihydroxyphenyl)acrylate (6)

Caffeic acid (4) (2.0 g 11.1 mmol) was dissolved in MeOH then catalytic amount of H$_2$SO$_4$ was added. The reaction mixture was stirred for 1 h at r.t. Then the solvent was removed under reduced pressure. The crude was dissolved in DMF and NaH (1.7 g 44.1 mmol) and MOMCl (3.1 ml 39.2 mmol) were added at 0° C. The reaction mixture was stirred for overnight. The reaction was quenched with saturated ammonium chloride solution. Then the reaction mixture was extracted with ether and water and the ether layer was dried over sodium sulphate. The solvent was removed under reduced pressure and crude was purified by column chromatography using ethyl acetate and hexane to give 6 (3.0 g, 95%). $^1$H NMR (500 MHz, CDCl$_3$): δ 3.51 (3H, s), 3.53 (3H, s), 3.79 (3H, s), 5.25 (2H, s), 5.27 (3H, s), 6.33 (1H, d, J=15.8 Hz), 7.15 (2H, s), 7.36 (1H, s), 7.62 (1H, d, J=15.8 Hz). $^{13}$C NMR: (125 MHz, CDCl$_3$) δ 51.5, 56.2, 56.2, 95.0, 95.4, 115.5, 116.0, 116.2, 123.3, 128.7, 144.3, 147.3, 149.0, 167.4. ESIMS: m/z 305 [M+Na]$^+$.

Example-3

(E)-3-(3,4-bis(methoxymethoxy)phenyl)acrylic acid (7)

Compound (6) (3.5 g 12.4 mmol) was dissolved in MeOH and THF and NaOH (1.48 g 37.2 mmol) was added. The reaction mixture was stirred for overnight. The solvent was removed under reduced pressure extracted with ethyl acetate and water, and washed with 1N HCl. The organic layer was dried over Na$_2$SO$_4$. The solvent was removed under reduced pressure to give 7 (3.2 g, 96%). $^1$H NMR: (500 MHz, CDCl$_3$) δ 3.52 (3H, s), 3.53 (3H, s), 5.27 (2H, s), 5.28 (2H, s), 6.34 (1H, d, J=15.8 Hz), 7.18 (2H, s), 7.40 (1H, s), 7.7 (1H, d, J=15.8 Hz). $^{13}$C NMR: (125 MHz, CDCl$_3$) δ 56.2, 56.3, 95.0, 95.4, 115.7, 115.7, 116.0, 123.8, 128.4, 146.5, 147.3, 149.4, 172.3. ESI-MS: m/z 291 [M+Na]$^+$.

Example-4

(E)-3-(3,4-bis(methoxymethoxy)phenyl)-1-(2,4,6-tris(methoxymethoxy) phenyl)prop-2-en-1-one (8)

Compound (7) (1.0 g 3.7 mmol) was dissolved in DCM then TFAA (0.78 ml 3.7 mmol) was added drop wise at −5° C., and stirred for 5 min. Then compound 5 (1.1 g 4.4 mmol) in DCM was added at −5° C. The reaction mixture was quenched with saturated ammonium chloride solution after 30 min. the reaction mixture was extracted with ethyl acetate and water. The organic layer was dried over Na$_2$SO$_4$, and solvent was removed under reduced pressure. The crude was purified by column chromatography using ethyl acetate and hexane to give compound 8 (1.0 g, 55%). $^1$H NMR: (300 MHz, CDCl$_3$) δ 3.39 (6H, s). 3.51 (9H, s), 5.11 (4H, s), 5.19 (2H, s), 5.22 (2H, s), 5.25 (2H, s), 5.27 (2H, s), 6.58 (2H, s), 6.87 (1H, d, J=16.0 Hz), 7.16 (2H, d), 7.28 (1H, d, J=16.0 Hz), 7.37 (1H, s). $^{13}$C NMR: δ 56.2, 94.4, 94.5, 95.0, 95.4, 97.0, 114.7, 115.7, 116.0, 123.6, 127.8, 129.1, 144.8, 147.3, 149.2, 155.6, 159.5, 194.2. ESI-MS: m/z 509 [M+H]$^+$.

Example-5

(3(3,4bis(methoxymethoxy)phenyl) oxiran2yl) (2,4,6 tris (methoxymethoxy) phenyl) methanone (9)

To a stirring solution of (8) (2 g, 3.9 mmol) in 60 ml of MeOH was added, 3.0 ml of 2N NaOH solution and 3.0 mL of 30% H$_2$O$_2$. The reaction was stirred at room temperature for 5 h, The reaction was then evaporated, the residue was partitioned between 50 ml of water and ethyl acetate, the organic layer was dried (Na$_2$SO$_4$), filtrated, and the resulted solution was subjected to next step directly.

Example-6

2-(3,4-dihydroxyphenyl)-3,5,7-trihydroxychroman-4-one (15), viz (+/−)-taxifolin (10)

To a stirred solution of above mentioned epoxide (9) (2.0 g, 3.8 mmol) in 60 ml of MeOH and 20 mL of THF were added concentrated HCl (1.0 ml) and MeOH (5.0 ml). The reaction was maintained at 55° C. for 2 h. After evaporation of most of the solvent, the mixture was extracted by ethyl acetate. The organic layer was washed successively by water and brine, dried (Na$_2$SO$_4$), and filtered. The filtrate was evaporated to give the residue which was subjected to a column chromatography with CHCl$_3$/MeOH 10:1 to give 0.84 g of (10) as pale yellow solid. Yield 73%; $^1$H NMR (400 MHz, CD$_3$OD): δ 4.50 (1H, d, J=12.0 Hz), 4.90 (1H, d, J=12.0 Hz), 5.88 (1H, d, J=2.0 Hz), 5.92 (1H, d, J=2.0 Hz) 6.78-6.83 (2H, m), 6.96 (1H, d, J=2.1 Hz). $^{13}$C NMR: (CD$_3$OD, 125 MHz) δ 73.66, 85.10, 96.2, 97.3, 101.8, 115.8, 120.8, 129.8, 146.4, 147.1, 164.3, 165.3, 168.6, 198.4. ESI-MS: m/z 327 [M+Na]$^+$.

Example-7

(2S,3S)-(+)-3',4',5,7-tetrahydroxydihydroflavonol-6-C-β-D-glucopyranoside (1)

Yield: 0.268 g. (35%); amorphous; [α]$_D^{26}$+1.23° (c, 0.27; MeOH) {lit [α]$_D^{25}$+1.33° (c, 0.098; MeOH), *Bioorg. Med. Chem. Lett.* 2009, 19, 4684-4687}; FAB-MS: m/z 467 [M+1]$^+$; C$_{21}$H$_{22}$O$_{12}$; $^1$H NMR: (DMSO-d$_6$, 500 MHz) δ 4.96 (1H, d, J=10.9 Hz, H-2), 4.50 (1H, m, H-3), 5.92 (1H, s, H-8), 6.89 (1H, s, H-5'), 6.76 (2H, s, H-2', 6'), 4.87 (1H, m, H-1" along with OH signal), 3.14 (2H, m, H-2", 5"), 3.42 (1H, m, H-3"), 3.68 (1H, m, H-4"), 4.01 (1H, m, H-6"a), 4.48 (1H, m, H-6"b), 12.51 (1H, s, OH-5), 9.07 (1H, s, OH-3), 9.02 (1H, s, OH-3'), 4.87 (1H, brs, OH), 4.62 (1H, brs, OH), 4.49 (1H, brs, OH). $^{13}$C NMR: (DMSO-d$_6$, 125 MHz) δ 82.9 (C-2), 71.6 (C-3), 198.0 (C-4), 162.6 (C-5), 106.0 (C-6), 166.0 (C-7), 94.7 (C-8), 161.3 (C-9), 100.2 (C-10), 128.0 (C-1'), 115.3 (C-2'), 145.8 (C-3'), 145.0 (C-4'), 115.1 (C-5'), 119.4 (C-6'), 72.9 (C-1"), 70.7 (C-2"), 79.1 (C-3"), 70.3 (C-4"), 81.6 (C-5"), 61.6 (C-6").

Example-8

(2R,3R)-(+)-3',4',5,7-tetrahydroxydihydroflavonol-6-C-β-D-glucopyranoside (2)

Yield: 0.160 g. (35%); amorphous; [α]$_D^{26}$+8.53° (c, 1.0; MeOH); {lit (*J. Agric. Food Chem.* 2012, 60, 2053-2062)} FAB-MS: m/z 467 [M+1]$^+$; C$_{21}$H$_{22}$O$_{12}$; $^1$H NMR: (DMSO-d$_6$, 500 MHz) δ 4.94 (1H, d, J=10.3 Hz, H-2), 4.52 (1H, d, J=10.3 Hz, H-3), 5.92 (1H, s, H-8, 6.86 (1H, s, H-5'), 6.73 (2H, s, H-2', 6'), 4.74 (1H, m, H-1" along with OH signal), 3.14 (2H, m, H-2", 5"), 3.46 (1H, m, H-3"), 3.67 (1H, m, H-4"), 3.96 (1H, m, H-6"a), 4.41 (1H, m, H-6"b), 12.43 (1H, s, OH-5), 8.86 (2H, s, OH-3 and OH-3'), 5.74 (1H, d, J=5.9 Hz, OH), 4.47 (1H, m, OH), 4.41 (1H, m, OH), 4.34 (1H, m, OH). $^{13}$C NMR: (DMSO-d$_6$, 75 MHz) δ 83.2 (C-2), 71.7 (C-3), 197.9 (C-4), 162.7 (C-5), 105.8 (C-6), 166.2 (C-7), 95.0 (C-8), 161.6 (C-9), 100.3 (C-10), 128.1 (C-1'), 115.5 (C-2'), 145.9 (C-3'), 145.1 (C-4'), 115.3 (C-5'), 119.9 (C-6'), 73.1 (C-1"), 70.6 (C-2"), 79.0 (C-3"), 70.3 (C-4"), 81.3 (C-5"), 61.6 (C-6").

We claim:

1. A process for total synthesis of flavonoid compound of formula I and isomers thereof,

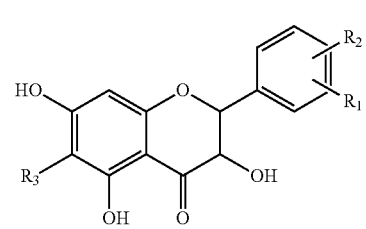

wherein R$_1$ and R$_2$ is OH; R$_3$=H, or

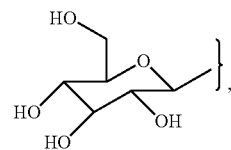

the process comprising the steps of:
  i. protecting the hydroxyl groups of phloroglucinol and hydroxyl groups of caffeic acid as ethers by using a protecting group and a base in a solvent to get 1,3,5-tris(methoxymethoxy) benzene (5) and (E)-methyl3-(3,4-dihydroxyphenyl) acrylate (6) respectively;

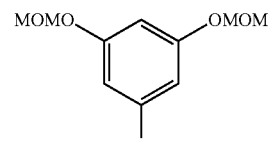

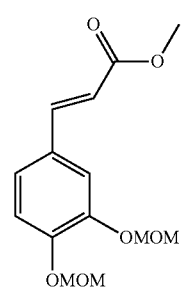

where MOMO is methoxymethoxy and OMOM is also methoxymethoxy;
  ii. hydrolyzing of the (E)-methyl 3-(3,4-dihydroxyphenyl) acrylate (6) obtained in step (i) by using a hydrolyzing agent to get (E)-3-(3,4-bis(methoxymethoxy) phenyl) acrylic acid (7);

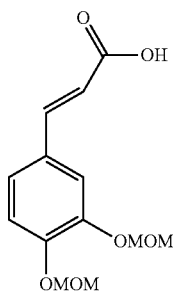

7 iii. acylating the 1,3,5-tris(methoxymethoxy)benzene (5) and (E)-3-(3,4-bis (methoxymethoxy) phenyl)acrylic acid (7) obtained in steps (i & ii) in presence of an acylating agent in a solvent at a temperature ranging between −5° C. to 0° C. to get (E)-3-(3,4-bis (methoxymethoxy)phenyl)-1-(2,4,6-tris (methoxymethoxy)phenyl) prop-2-en-1-one (8);

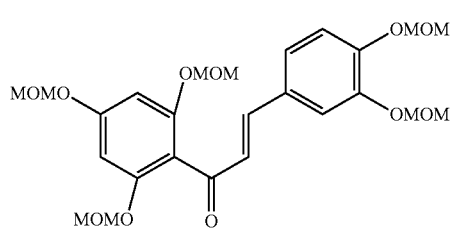

8 iv. oxidizing (E)-3-(3,4-bis(methoxymethoxy)phenyl)-1-(2,4,6-tris(methoxymethoxy) phenyl)prop-2-en-1-one (8) obtained in step (iii) with an oxidizing agent to get racemic epoxide ((3-(3,4-bis(methoxymethoxy)phenyl)oxiran-2-yl)(2,4,6-tris(methoxymethoxy)phenyl) methanone) (9);

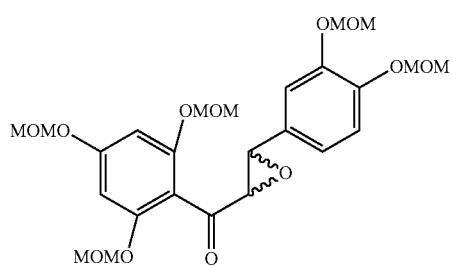

9 v. reacting the epoxide compound ((3-(3,4-bis (methoxymethoxy)phenyl)oxiran-2-yl)(2,4,6-tris (methoxymethoxy) phenyl)methanone) (9) obtained in step (iv) by using excess of acid in different ratio of mixture of solvent ranging in the ratio of 0:1/1:0 to 5:1/1:5 to obtain racemic taxifolin 2-(3,4-dihydroxyphenyl)-3,5,7-trihydroxychroman-4-one(+/−Taxifolin) (10);

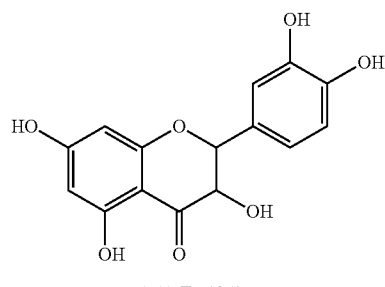

(+/−)-Taxifolin vi. optionally separating the racemic taxifolin 2-(3,4-dihydroxyphenyl)-3,5,7-trihydroxychroman-4-one(+/− Taxifolin) by chromatographic method to obtain (−) taxifolin and (+) taxifolin (11) and (12); and

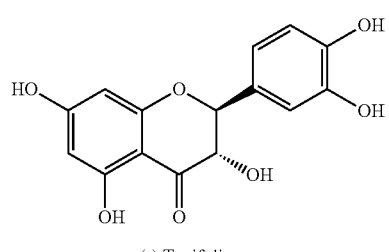

(−) Taxifolin

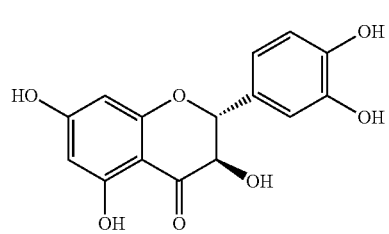

(+) Taxifolin vii. refluxing the racemic or (+)taxifolin or (−)taxifolin obtained in steps (v) and (vi) in a solvent and D-glucose in presence of a Lewis acid at a temperature ranging between 85° C. to 90° C. for a period ranging between 24 h to 48 hr to get diastereomeric mixture of taxifolin-glucopyranosides or (2R,3R)-Taxifolin-6-C-beta-D-Glucopyranoside or Ulmoside A respectively; separating the diastereomeric mixture of taxifolin-glucopyranosides to obtain (2R,3R) taxifolin-6-C-β-D-glucopyranoside (2) and (2S,3S) taxifolin-6-C-β-D-glucopyranoside (ulmoside A) pure product

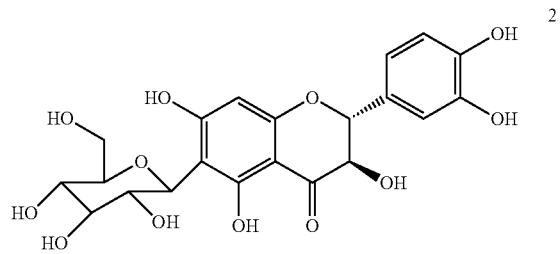

(2R,3R) Taxifolin-6-C-β-D-glucopyranoside

-continued

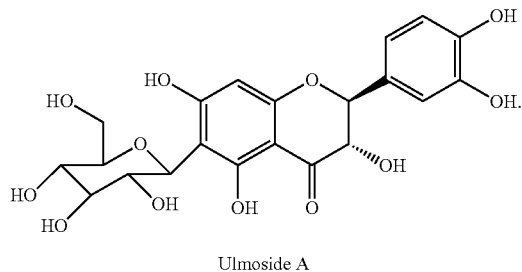

Ulmoside A

2. The process as claimed in claim 1, wherein the base is selected from the group consisting of NaH, NaNH$_2$, KH, KNH$_2$, MeONa, EtONa, iPrONa and t-BuOK.

3. The process as claimed in claim 1, wherein the acid is selected from the group consisting of ZnCl$_2$, BF$_3$.OEt$_2$ and Zr(OTf)$_2$.

4. The process as claimed in claim 1, wherein the reagent used for protecting hydroxyl group in step (i) is selected from the group consisting of methoxymethylchloride, 2-methoxyethoxymethyl chloride (or) 2-methoxyethylacetate, dimethoxymethane and t-butyldimethylsilyl chloride, t-butyldiphenylsilyl chloride.

5. The process as claimed in claim 1, wherein the solvent used in step (I) is selected from the group consisting of DMF, THF, Et$_2$O, 1,4 dioxane, diisopropylether and t-Butyl ethyl ether.

6. The process as claimed in claim 1, wherein the hydrolyzing agent is selected from the group consisting of NaOH, KOH, LiOH, Cs$_2$CO$_3$ in a solvents like MeOH, EtOH, iPrOH, MeOH/THF, EtOH/THF and Dioxane/H$_2$O.

7. The process as claimed in claim 1, wherein the acylating agent used is TFAA(trifluroaceticanhydride).

8. The process as claimed in claim 1, wherein the solvent used in step (iii) for acylating agent is selected from the group consisting of DCM (Dichloromethane), DOE (1,2-dichloroethane) and CCl$_4$.

9. The process as claimed in claim 1, wherein the oxidation of compound is done by using the reagent comprising of hydrogen peroxide and a base selected from the group consisting of NaOH, KOH, TBHP (tert-Butyl hydroperoxide) in presence of NaH or DBU (1,8-Diazabicyclo[5.4.0]undec-7-ene) or KH.

10. The process as claimed in claim 1, wherein the acid used in step (v) is selected from the group consisting of concentration HCl and H$_2$SO$_4$.

11. The process as claimed in claim 1, wherein the solvent used in step (v) is selected from the group consisting of MeOH, EtOH, iPrOH, MeOH, EtOH, THF and mixture thereof.

12. The process as claimed in claim 1, wherein different ratio of mixture of solvent used in step (vi) is selected from the group essentially consisting of CH$_3$CN/H$_2$O, EtOH/H$_2$O, THF/H$_2$O, DMF/H$_2$O, iPrOH/H$_2$O or single solvent is selected from the group essentially consisting of CH$_3$CN, EtOH, DMF, THF, MeOH, H$_2$O, iPrOH.

13. The process as claimed in claim 1, wherein the Lewis acid is M(X)$_3$ wherein M comprises La, Ce, Pr, Nd, Sm, Eu, Gd, Tb, Dy, Ho, Er, Tm, Sc, Cd, Fe, Al, Cr, Co, Ni, Cu, Zn, Rh, Ag and X=OTf, Cl, ClO$_4$.

14. The process as claimed in claim 1, wherein the chromatographic method used for separation for distereomeric mixture of taxifolin or taxifolin-glucopyranosides is selected from the group consisting of HPLC, UPLC, UFLC and MPLC.

15. The process as claimed in claim 1, wherein the representative flavonoid compounds prepared by the process comprising:

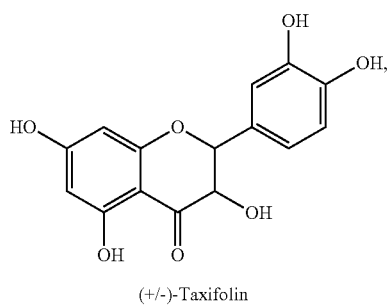

(+/-)-Taxifolin

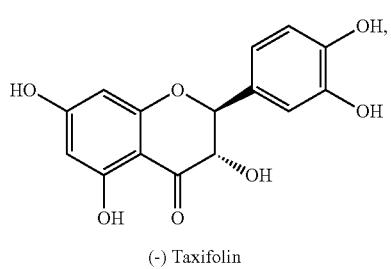

(-) Taxifolin

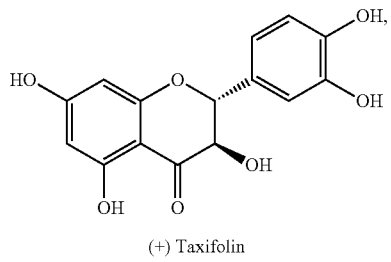

(+) Taxifolin

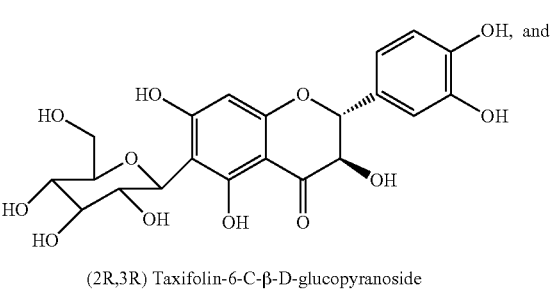

(2R,3R) Taxifolin-6-C-β-D-glucopyranoside

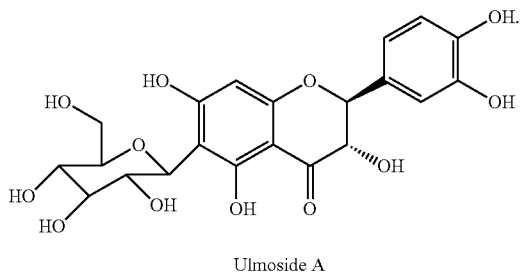

Ulmoside A

* * * * *